United States Patent [19]

McConlogue et al.

[11] Patent Number: 5,604,102
[45] Date of Patent: Feb. 18, 1997

[54] METHODS OF SCREENING FOR β-AMYLOID PEPTIDE PRODUCTION INHIBITORS

[75] Inventors: Lisa C. McConlogue, San Francisco; Dale B. Schenk, Pacifica; Peter A. Seubert, South San Francisco; Sukanto Sinha, San Francisco; Jun Zhao, La Jolla, all of Calif.

[73] Assignee: Athena Neurosciences, Inc., South San Francisco, Calif.

[21] Appl. No.: 143,697

[22] Filed: Oct. 27, 1993

Related U.S. Application Data

[63] Continuation-in-part of Ser. No. 965,971, Oct. 26, 1992, Pat. No. 5,441,870, which is a continuation-in-part of Ser. No. 868,949, Apr. 15, 1992, abandoned.

[51] Int. Cl.$^6$ .......................... C12N 15/00; G01N 33/53; G01N 33/567; A61K 49/00
[52] U.S. Cl. .......................... 435/7.1; 424/9.2; 435/7.21; 435/172.3; 800/2; 530/350
[58] Field of Search .......................... 435/6, 7.1; 800/2; 530/350; 424/9

[56] References Cited

U.S. PATENT DOCUMENTS

| | | | |
|---|---|---|---|
| 4,666,829 | 5/1987 | Glenner et al. | 435/6 |
| 5,134,062 | 7/1992 | Blass | 435/7.21 |
| 5,200,339 | 4/1993 | Abraham | 435/23 |
| 5,234,814 | 8/1993 | Card et al. | 435/7.21 |

FOREIGN PATENT DOCUMENTS

| | | |
|---|---|---|
| 123527 | 10/1984 | European Pat. Off. . |
| 171496 | 2/1986 | European Pat. Off. . |
| 173494 | 3/1986 | European Pat. Off. . |
| 184187 | 6/1986 | European Pat. Off. . |
| 62-100291 | 5/1987 | Japan . |
| WO86/01533 | 3/1986 | WIPO . |
| WO87/02671 | 5/1987 | WIPO . |
| WO91/16628 | 10/1991 | WIPO . |
| 9119810 | 12/1991 | WIPO . |
| WO92/00521 | 1/1992 | WIPO . |
| WO92/09699 | 6/1992 | WIPO . |

OTHER PUBLICATIONS

Mullon et al Nature Genetics 1:345, 1992.
Goding is Monoclonal Antibodies: Principles & Practice, Chapter 3, pp. 56–74, 1984.
Goate et al. (1991) Nature 349:704–706.
Chartier Harlan et al., (1991) Nature 353:844–846.
Kitaguchi et al. (1988) Nature 331:530–532.
Mullan et al. (1992) Nature Genet 1:345–347.
Glenner and Wong (1984) Biochem. Biophys. Res. Commun. 120:885–890.
Kang et al. (1987) Nature 325:733–736.
Ponte et al. (1988) Nature 331:525–527.
Esch et al. (1990) Science 248:1122–1124.
Weidemann et al. (1989) Cell 57:115–126.
Oltersdorf et al. (1990) J. Biol. Chem. 265:4492–4497.
Robakis et al. Soc. Neurosci. Oct. 26, 1993, Abstract No. 15.4, Anaheim, CA.
Murrell et al. (1991) Science 254:97–99.
Golde et al. (1992) Science 225:728–730.
Estus et al. (1992) Science 255:726–728.
Kennedy et al. (1992) Neurodegeneration 1:59–64.
Haass et al. (1992) Nature 359:322–325.
Seubert et al. (1992) Nature 359:325–327.
Palmert et al. (1989) Biochem. Biophys. Res. Comm. 165:182–188.
Palmert et al. (1989) Proc. Natl. Acad. Sci USA 86:6338–6342.
Abraham et al. (1991) Biochem. Biophys. Res. Comm. 174:790–796.
Hyman et al. (1992) J. Neuropath. Exp. Neurol. 51:76.
Pulliman et al. (1984) J. Virol. Met. 9:301.
Forss–Petter et al. (1990) Neuron 5:187–197.
Seubert et al. (1993) Nature 361:260–263.
Glenner and Wong (1984) Biochem. Biophys. Res. Commun. 122:1131–1135.
Selkoe et al. (1988) Proc. Natl. Acad. Sci. USA 85:7341.
Oltersdorf et al. (1989) Nature 341:144.
J. W. Goding, "Monoclonal antibodies: Principles and Practice", (1983) Academic Press, London, pp. 56–75.

*Primary Examiner*—Suzanne E. Ziska
*Attorney, Agent, or Firm*—Townsend and Townsend and Crew

[57] ABSTRACT

Processing of β-amyloid precursor protein (βAPP) is monitored by detecting the secretion of a soluble amino-terminal fragment or βAPP (ATF-βAPP) resulting from cleavage of βAPP at the amino-terminus of β-amyloid peptide. Secretion of ATF-βAPP in animal models may be monitored to identify inhibitors of β-amyloid production. The ATF-βAPP may be detected using antibodies and other specific binding substances which recognize a carboxy terminal residue on the fragment. Animals expressing the Swedish mutation of βAPP are described which produce abundant amounts of ATF-βAPP.

19 Claims, 8 Drawing Sheets

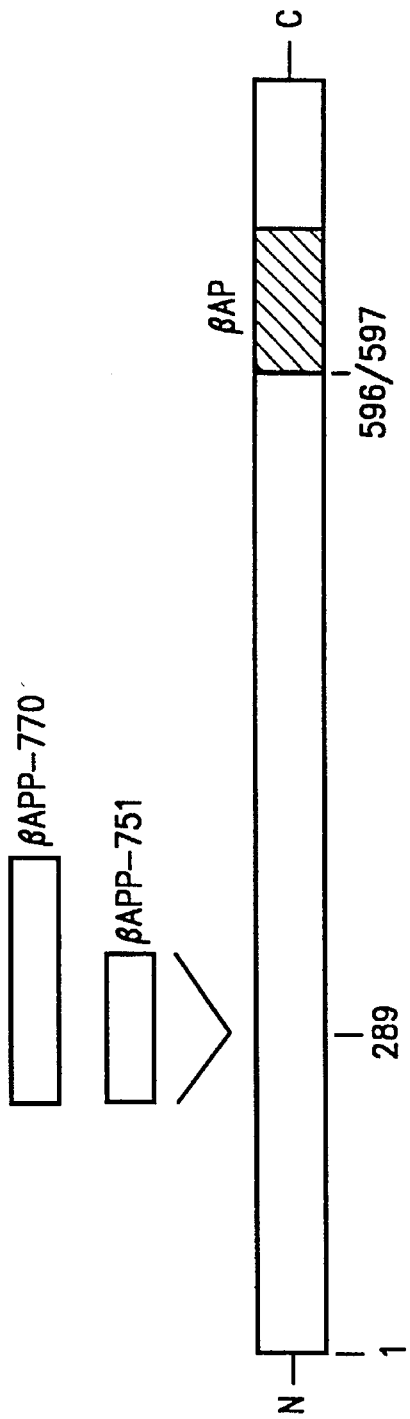
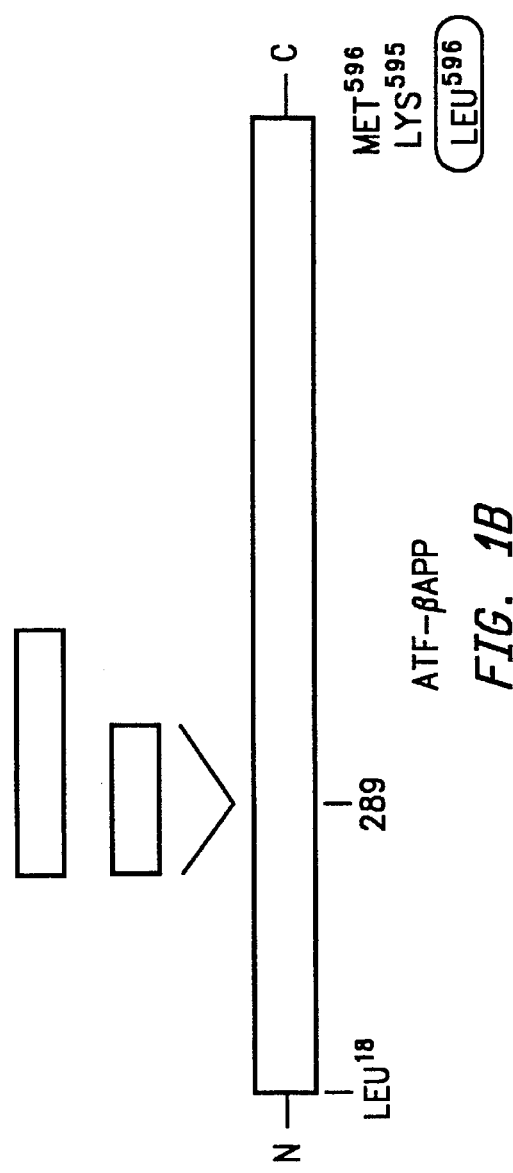

METHODS OF SCREENING FOR β-AMYLOID PEPTIDE PRODUCTION INHIBITORS

CROSS-REFERENCE TO RELATED APPLICATION

This application is a continuation-in-part of application Ser. No. 07/965,971, filed Oct. 26, 1992, U.S. Pat. No. 5,441,870, which was a continuation-in-part of application Ser. No. 07/868,949, filed Apr. 15, 1992, now abandoned the disclosures of which are specifically incorporated herein by reference.

BACKGROUND OF THE INVENTION

1. Field of the Invention

The present invention relates generally to methods and compositions for monitoring the processing of β-amyloid precursor protein. More particularly, the present invention relates to the use of such methods and compositions for the diagnosis, prognosis, and monitoring response to therapy of Alzheimer's disease, and for screening and evaluation of potential drugs for the treatment of Alzheimer's disease.

Alzheimer's disease is characterized by the presence of numerous amyloid plaques and neurofibrillary tangles (highly insoluble protein aggregates) present in the brains of Alzheimer's disease patients, particularly in those regions involved with memory and cognition. While in the past there was significant scientific debate over whether the plaques and tangles are a cause or are merely the result of Alzheimer's disease, recent discoveries indicate that amyloid plaque is a causative precursor or factor. In particular, it has been discovered that the production of β-amyloid peptide, a major constituent of the amyloid plaque, can result from mutations in the gene encoding amyloid precursor protein, a protein which when normally processed will not produce the β-amyloid peptide. It is presently believed that a normal (non-pathogenic) processing of the β-amyloid precursor protein occurs via cleavage by a putative "α-secretase" which cleaves between amino acids 16 and 17 of the protein. It is further believed that pathogenic processing occurs via a putative "β-secretase" at the amino-terminus of the β-amyloid peptide within the precursor protein.

The identification of mutations in the amyloid precursor protein gene which cause familial, early onset Alzheimer's disease is the strongest evidence that amyloid metabolism is the central event in the pathogenic process underlying the disease. Four reported disease-causing mutations include with respect to the 770 isoform, valine[717] to isoleucine (Goate et al. (1991) Nature 349:704–706), valine[717] to glycine (Chartier Harlan et al. (1991) Nature 353:844–846, valine[717] to phenylalanine (Murrell et al. (1991) Science 254:97–99) and with respect to the 695 isoform, a double mutation changing lysine[595]-methionine[596] to asparagine[595]-leucine[596] (Mullan et al. (1992) Nature Genet 1:345–347) referred to as the Swedish mutation. Moreover, β-amyloid peptide appears to be toxic to brain neurons, and neuronal cell death is associated with the disease.

Thus, the ability to monitor cellular processing of the amyloid precursor protein would be of significant value in the diagnosis, prognosis, and therapeutic supervision of Alzheimer's disease. In particular, it would be desirable to identify minimally invasive procedures for screening and evaluating detectable diagnostic markers in readily obtainable patient samples, such as serum, cerebrospinal fluid (CSF), and the like.

A number of potential diagnostic markers for Alzheimer's disease have been proposed. Of particular interest to the present invention are certain fragments of the amyloid precursor protein, including carboxy terminal fragments (such as the β-amyloid peptide itself and fragments thereof), and amino-terminal fragments (such as certain 25 kD, 105 kD, and 125 kD fragments). As yet, none of the proposed markers has proved to be definitive for the antemortem diagnosis or monitoring of Alzheimer's disease.

Thus, it would be desirable to identify additional and alternative diagnostic markers for Alzheimer's disease. Such markers should be useful by themselves and/or in combination with other diagnostic markers and procedures. Preferably, the diagnostic markers would be detectable in body fluids, such as CSF, blood, plasma, serum, urine, tissue, and the like, so that minimally invasive diagnostic procedures can be utilized.

Of further interest to the present invention are in vitro and in vivo systems and methods for screening candidate drugs for the ability to inhibit or prevent the production of β-amyloid plaque. It would be desirable to provide methods and systems for screening test compounds for the ability to inhibit or prevent the conversion of amyloid precursor protein to β-amyloid peptide. In particular, it would be desirable to base such methods and systems on metabolic pathways which have been found to be involved in such conversion, where the test compound would be able to interrupt or interfere with the metabolic pathway which leads to conversion. Such methods and systems should be rapid, economical, and suitable for screening large numbers of test compounds.

2. Description of the Background Art

β-amyloid peptide (also referred to as A4, βAP, Aβ, or AβP; see, U.S. Pat. No. 4,666,829 and Glenner and Wong (1984) Biochem. Biophys. Res. Commun. 120:1131–1135) is derived from β-amyloid precursor protein (βAPP), which is expressed in differently spliced forms of 695, 751, and 770 amino acids. See, Kang et al. (1987) Nature 325:773–776; Ponte et al. (1988) Nature 331:525–527; and Kitaguchi et al. (1988) Nature 331:530–532. Normal processing of amyloid precursor protein involves proteolytic cleavage at a site between residues Lys[16] and Leu[17] (as numbered for the vAP region where Asp[597] is residue 1 in Kang et al. (1987)), supra, near the transmembrane domain, resulting in the constitutive secretion of an extracellular domain which retains the remaining portion of the β-amyloid peptide sequence (Esch et al. (1990) Science 248:1122–1124). This pathway appears to be widely conserved among species and present in many cell types. See, Weidemann et al. (1989) Cell 57:115–126 and Oltersdorf et al. (1990) J. Biol. Chem. 265:4492–4497. This normal pathway cleaves within the region of the precursor protein which corresponds to the β-amyloid peptide, thus apparently precluding its formation. Another constitutively secreted form of βAPP has been noted (Robakis et al. Soc. Neurosci. Oct. 26, 1993, Abstract No. 15.4, Anaheim, Calif.) which contains more of the βAP sequence carboxy terminal to that form described by Esch et al. supra.

Golde et al. (1992) Science 255:728–730, prepared a series of deletion mutants of amyloid precursor protein and observed a single cleavage site within the β-amyloid peptide region. Based on this observation, it was postulated that β-amyloid peptide formation does not involve a secretory pathway. Estus et al. (1992) Science 255:726–728, teaches that the two largest carboxy terminal proteolytic fragments of amyloid precursor protein found in brain cells contain the entire β-amyloid peptide region.

PCT application. WO 92/00521 describes methods for evaluating Alzheimer's disease based on measuring the amounts of certain 25 kD, 105 kD, and 125 kD soluble derivatives of amyloid precursor protein in a patient's cerebrospinal fluid. FIG. 3 of WO 92/00521 suggests that cleavage of amyloid precursor protein may occur adjacent to the amino-terminus of β-amyloid peptide to produce a soluble amino-terminal fragment, but no evidence or discussion of such cleavage is presented in the application. Kennedy et al. (1992) Neurodegeneration 1:59–64, present data for a form of secreted βAPP, which was characterized by its reactivity with antibodies to residues 527–540 of βAPP and the lack of reactivity with antibodies to the first fifteen residues of βAP. No direct evidence is provided to suggest the cleavage site or identity of the carboxy terminus of the βAPP form. PCT application WO 91/16628 describes methods for diagnosing disease based on detection of amyloid precursor proteins and fragments thereof utilizing antibodies to protease nexin-2 or amyloid precursor protein.

Recent reports show that soluble β-amyloid peptide is produced by healthy cells into culture media (Haass et al. (1992) Nature 359:322–325) and in human and animal CSF (Seubert et al. (1992) Nature 359:325–327).

Palmert et al. (1989) Biochm. Biophys. Res. Comm. 65:182–188, describes three possible cleavage mechanisms for βAPP and presents evidence that βAPP cleavage does not occur at methionine$^{596}$ in the production of soluble derivatives of βAPP. U.S. Pat. No. 5,200,339, discusses the existence of certain proteolytic factor(s) which are putatively capable of cleaving βAPP at a site near the βAPP amino-terminus.

SUMMARY OF THE INVENTION

Methods and compositions are provided for detecting and monitoring an amino-terminal fragment of β-amyloid precursor protein (βAPP) resulting from β-secretase cleavage. The resulting fragment, referred to hereinafter as ATF-βAPP, may be detected in biological samples and is useful for monitoring the processing of βAPP in animal models. In particular, the present invention provides for monitoring of βAPP processing in vivo where the presence of the ATF-βAPP is detected in a specimen from an animal transformed to express the Swedish mutation of human βAPP and where the ATF-βAPP has been cleaved from βAPP between LEU$^{596}$ and ASP$^{597}$, based on the numbering of Kang, et al., supra, in the 695 amino acid isoform. The Swedish mutation results from a substitution of ASN$^{595}$-LEU$^{596}$ for LYS$^{595}$-MET$^{596}$ which are present in the wild type 695 isoform of βAPP.

It has been found that animal models expressing the human Swedish mutation of the βAPP gene are particularly prolific producers of the amino-terminal fragment thereof. That is, non-human animal models are able to cleave the human Swedish mutation at a greater frequency than cleavage of either the endogenous βAPP or the wild type human βAPP. It is further believed that intracellular processing of the Swedish mutation of human βAPP results in greater production of the ATF-βAPP than is produced by other human mutations of the βAPP gene. Thus, transgenic animal systems, such as transgenic mice, expressing the Swedish mutation of βAPP are particularly suitable as models for monitoring intracellular processing of βAPP as well as for screening test compounds for the ability to inhibit or modulate cleavage of βAPP as a result of β-secretase activity, the apparently pathogenic form of βAPP processing.

In a preferred aspect of the present invention, ATF-βAPP produced by β-secretase cleavage of the Swedish mutation of βAPP is detected by a binding substance which specifically binds to an epitope present at or near the carboxy-terminus of ATF-βAPP, where the epitope comprises the carboxy terminal residue (LEU$^{596}$), and preferably the five amino acid residues which are present at the carboxy terminus of ATF-βAPP. It has been found that binding between binding substances, such as antibodies, against such a C-terminal epitope provides for high specificity detection of the Swedish form of ATF-βAPP. Preferred antibodies are raised against a peptide comprising the five-residue carboxy terminus which is exposed by β-secretase cleavage of the Swedish βAPP.

In another preferred aspect of the present invention, β-amyloid production inhibitors may be identified in transgenic animal models as described above. The animals are exposed to test compound(s) and those compounds which affect, usually by diminishing, the production of ATF-βAPP are considered candidates for further testing as drugs for the treatment of βAP-related conditions.

In yet another aspect of the present invention, antibodies are provided which are specific for the amino-terminal fragment of Swedish βAPP. Preferably, the antibodies are raised against a peptide comprising the amino-terminal residues of the Swedish ATF-βAPP, and the antibodies may be polyclonal or monoclonal.

BRIEF DESCRIPTION OF THE DRAWINGS

FIGS. 1A and 1B illustrate the various isoforms of normal βAPP and the corresponding isoforms of ATF-βAPP, respectively.

DESCRIPTION OF THE SPECIFIC EMBODIMENTS

Figures 2A, 2B, 2C:
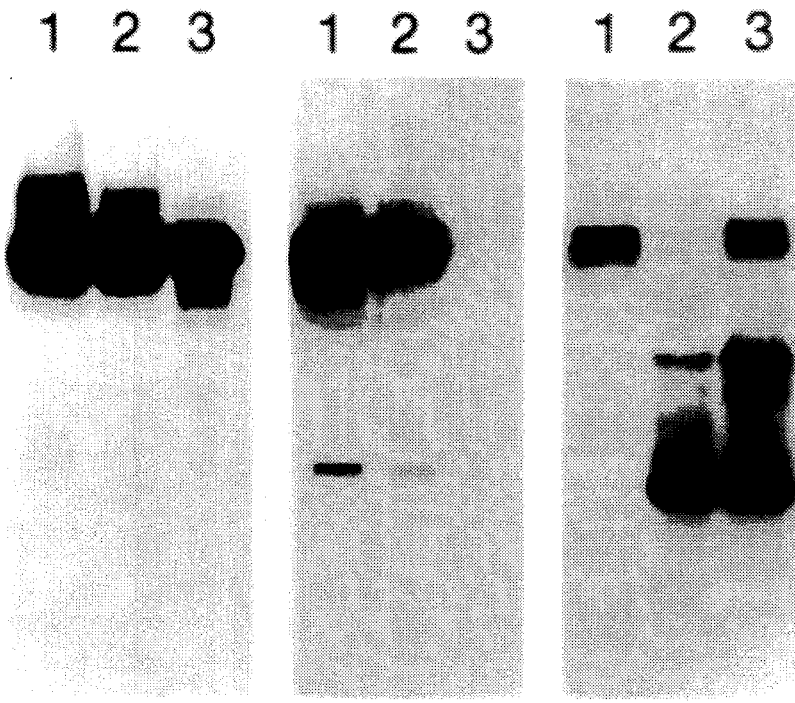
FIGS. 2A, 2B, and 2C, are chemiluminescent gel patterns of material derived from conditioned medium of a human fetal brain cell culture. Lanes 1, 2, and 3 of each gel represent the untreated conditioned medium, the conditioned medium depleted by reaction with antibody which recognizes an epitope within the β-amyloid peptide residues 1–16, and the material removed by this antibody, respectively. Panels A, B, and C represent the following probes: anti-5 antibody (which recognizes locations on βAPP amino-terminal to β-amyloid peptide region), antibody 92 (which was raised against a synthetic peptide terminating in the C-terminal methionine exposed by cleavage of βAP from βAPP), and antibody 10D5 (a monoclonal antibody which recognizes an epitope of βAP within residues 1–16), respectively.

The present invention results from the identification of a novel secreted fragment of β-amyloid precursor protein (βAPP) which results from cleavage of an intact β-amyloid peptide (βAP) region from the precursor protein. The novel secreted fragments comprise the amino-terminal portion of βAPP which remains after such cleavage and will be referred to hereinafter as the amino-terminal fragment form of βAPP (ATF-βAPP). ATF-βAPP is believed to be the product of an alternative secretory processing pathway for βAPP, which pathway is present even in normal (non-diseased) cells. It is further believed, however, that the alternate secretory pathway may be responsible for an essential event in the production of βAP in diseased cells in patients, and that abnormal production of ATF-βAPP may be involved in diseases related to βAP plaque, particularly Alzheimer's disease and Down's syndrome. Thus, the present invention provides methods and compositions for monitoring the cellular processing of βAPP based on the detection and measurement of ATF-βAPP in biological samples.

ATF-βAP is identified and recognized by specific binding to antibodies raised against peptides comprising certain residues of βAPP which lie immediately adjacent to the βAP region and for normal βAPP include the carboxy terminal methionine (numbered as methionine$^{596}$ in the 695 isoform, as set forth below). The peptides will usually include at least five contiguous residues up to and including residue$^{596}$, and specific methods for producing such antibodies are set forth below.

Referring now to FIGS. 1A and 1B, βAPP is found in three isoforms comprising 695, 751, and 770 amino acids, respectively. The 695 isoform is the most common in neuronal cells, with the 751 and 770 isoforms resulting from insertions at residue 289 on the 695 isoform (all numbering of the 695 isoform will be in accordance with Kang et al. (1987) Nature 325:733–736). ATF-βAPP apparently results from proteolytic cleavage of the various βAPP isoforms at or within the five residues on the amino-terminal side of the amino-terminus of the β-amyloid peptide (βAP) region, which is located between residues 596 and 597 of the 695 isoform. Such cleavage results in the exposure of a C-terminal residue, which will usually be methionine$^{596}$ lysine$^{595}$ or leucine$^{596}$, more usually being methionine$^{596}$ or leucine$^{596}$ shown as MET$^{596}$ and LEU$^{596}$ in FIG. 1B. Exposure of LEU$^{596}$ occurs with β-secretase cleavage of the Swedish mutation of human βAPP in both humans and animal models, as described in more detail hereinbelow. It will be appreciated, of course, that the C-terminal residues would have a different numbering when the ATF-βAPP is derived from a different βAPP isoform. In particular, the C-terminal methionine would be MET$^{652}$ and MET$^{671}$ and the C-terminal leucine would be LEU$^{651}$ and LEU$^{670}$ in the 751 and 770 βAPP isoforms, respectively. As used hereinafter and in the claims, methionine$^{596}$, lysine$^{595}$, and leucine$^{596}$ will refer generally to corresponding residues in all other isoforms or variants of βAPP. Presently, it is believed that the N-terminal residue of ATF-βAPP is LEU$^{18}$ in all isoforms (based on processing of the amino-terminal end of βAPP in secreted forms which are cleaved within the βAP region).

According to the present invention, ATF-βAPP may be detected and/or measured in a variety of biological samples, including in vitro samples, such as conditioned medium from cultured cells, and patient and animal model samples, typically CSF, blood, serum, plasma, urine, tissue, and the like. Detection and measurement may be accomplished by any technique capable of distinguishing ATF-βAPP from other β-APP fragments which might be found in the sample. Conveniently, immunological detection techniques may be employed which utilize antibodies, antibody fragments, or other equivalent specific binding substances, which bind to an epitope characteristic of the ATF-βAPP and which are substantially free of cross-reactivity with other βAPP fragments. Of particular use are antibodies and other binding substances which bind to an epitope which comprises the C-terminal residue of ATF-βAPP which is exposed upon β-secretase cleavage of the βAP region, e.g., methionine$^{596}$ leucine$^{596}$ or lysine$^{595}$. It has been found that such C-terminal-specific antibodies are able to discriminate between the ATF-βAPP and related βAPP fragments. Alternatively, immunological detection techniques may be based on isolated and purified ATF-βAPP using conventional techniques. The preparation of both C-terminal residue-specific antibodies and purified and isolated ATF-βAPP are described hereinafter. Particularly suitable detection techniques include ELISA, Western blotting, radioimmunoassay, and the like.

Other techniques for detecting ATF-βAPP which do not require the use of ATF-βAPP specific antibodies and/or competing antigen may also be employed. For example, two-dimensional gel electrophoresis may be employed to separate closely related soluble fragments of βAPP. Antibodies cross-reactive with many or all of the fragments may then be used to probe the gels, with the presence of ATF-βAPP being identified based on its precise position on the gel. Other techniques for detection of ATF-βAPP are also well within the skill in the art. For example, the secreted βAPP species which contain the amino-terminal region of βAP can be immunologically removed from a sample to isolate ATF-βAPP (see FIG. 2A, lane 2 and FIG. 5, lanes 11 and 12), which can then be detected by any of several methods as discussed above.

Antibodies specific for an epitope characteristic of the wild type ATF-βAPP may be prepared against a suitable antigen or hapten comprising the C-terminal ATF-βAPP sequence including the methionine residue. Antibodies specific for an epitope characteristic of the Swedish mutation of ATF-βAPP may be prepared against a suitable antigen or hapten comprising the C-terminal ATF-βAPP sequence including the leucine residue at position 596. Conveniently, synthetic peptides may be prepared by conventional solid phase techniques, coupled to a suitable immunogen, and used to prepare antisera or monoclonal antibodies by conventional techniques. One suitable synthetic peptide consists of six residues of ATF-βAPP (ISEVKM) which are located on the immediate amino-terminal side of βAP and which may be coupled to an immunogen and used to prepare specific antibodies as described in detail in the Experimental section. Other suitable peptide haptens will usually comprise at least five contiguous residues within βAPP on the immediate amino-terminal side of βAP, and may include more than six residues (although a peptide including sixteen amino-terminal residues was found to yield antisera which was less specific). The carboxy terminal 25 residues of the normal ATF-βAPP are as follows (using the single letter amino acid designations).

| DRGLT | TRPGSGLTNI | KTEEISEVKM |
|---|---|---|
| 576 | 586 | 596 |

The carboxy terminal 25 residues of the Swedish mutation of βAPP are as follows:

| DRGLT | TRPGSGLTNI | KTEEISEVNL |
|---|---|---|
| 576 | 586 | 596 |

Synthetic polypeptide haptens may be produced by the well-known Merrifield solid-phase synthesis technique where amino acids are sequentially added to a growing chain (Merrifield (1963) J. Am. Chem. Soc. 85:2149–2156). The amino acid sequences may be based on the sequence of ATF-βAPP set forth above or may utilize naturally occurring or engineered mutant sequences. For example, the peptides mimicking Swedish mutant would have asparagine$^{595}$-leucine$^{596}$ substituted for lysine$^{595}$-methionine$^{596}$ and another substitution might include only the leucine$^{596}$ substitution for methionine$^{596}$. A preferred peptide comprises the carboxy terminal five amino acids of Swedish ATF-βAPP: SEVNL.

Once a sufficient quantity of polypeptide hapten has been obtained, it may be conjugated to a suitable immunogenic carrier, such as serum albumin, keyhole limpet hemocyanin, or other suitable protein carriers, as generally described in Hudson and Hay, *Practical Immunology*, Blackwell Scientific Publications, Oxford, Chapter 1.3, 1980, the disclosure of which is incorporated herein by reference.

Once a sufficient quantity of the immunogen has been obtained, antibodies specific for the C-terminal residue exposed upon cleavage of βAP from ATF-βAPP may be produced by in vitro or in vivo techniques. In vitro techniques involve exposure of lymphocytes to the immunogens, while in vivo techniques require the injection of the immunogens into a suitable vertebrate host. Suitable vertebrate hosts are nonhuman, including mice, rats, rabbits, sheep, goats, and the like. Immunogens are injected into the animal according to a predetermined schedule, and the animals are periodically bled with successive bleeds having improved titer and specificity. The injections may be made intramuscularly, intraperitoneally, subcutaneously, or the like, and an adjuvant, such as incomplete Freund's adjuvant, will be employed.

If desired, monoclonal antibodies can be obtained by preparing immortalized cell lines capable of producing antibodies having desired specificity. Such immortalized cell lines may be produced in a variety of ways. Conveniently, a small vertebrate, such as a mouse is hyperimmunized with the desired immunogen by the method just described. The vertebrate is then killed, usually several days after the final immunization, the spleen cells removed, and the spleen cells immortalized. The manner of immortalization is not critical. Presently, the most common technique is fusion with a myeloma cell fusion partner, as first described by Kohler and Milstein (1975) Nature 256:495–497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in *Antibodies: A Laboratory Manual,* Harlow and Lane, eds., Cold Spring Harbor Laboratory, 1988, the full disclosure of which is incorporated herein by reference.

In addition to monoclonal antibodies and polyclonal antibodies (antisera), the detection techniques of the present invention will also be able to use antibody fragments, such as F(ab), Fv, $V_L$, $V_H$, and other fragments. It will also be possible to employ recombinantly produced antibodies (immunoglobulins) and variations thereof as now well described in the patent and scientific literature. See, for example, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference. It would also be possible to prepare other recombinant proteins which would mimic the binding specificity of antibodies prepared as just described.

The present invention further comprises isolated and purified ATF-βAPP, usually obtained in substantially pure form. "Substantially pure" means at least about 50% w/w (weight/weight) or more purity with substantial freedom from interfering proteins and contaminants. Preferably, the ATF-βAPP will be isolated or synthesized in a purity greater than 50% w/w, preferably being 80% w/w or higher. The ATF-βAPP may be purified from a natural source by conventional protein purification techniques, with homogeneous compositions of at least about 50% w/w purity being purified by use of antibodies prepared as described above using conventional immunoaffinity separation techniques. Suitable natural starting materials include conditioned medium from ATF-βAPP-producing cell lines, such as fetal brain cell cultures, and the like. Alternatively, the ATF-βAPP may be isolated from biological samples obtained from a human host, such as CSF, serum, and the like. Suitable protein purification techniques are described in *Methods in Enzymology,* Vol. 182, Deutcher, ed., Academic Press, Inc., San Diego, 1990, the disclosure of which is incorporated herein by reference.

Antibodies and purified ATF-βAPP prepared as described above can be used in various conventional immunological techniques for detecting ATF-βAPP in biological samples, particularly patient samples and animal specimens for the monitoring of β-amyloid-related diseases and drug screening, and in conditioned media from cell culture for monitoring the intracellular processing of βAPP. Suitable immunological techniques include immunoassays, such as ELISA, Western blot analyses, and the like. Numerous specific immunological detection techniques are described in Harlow and Lane, supra.

Detection of ATF-βAPP in patient samples can be used for diagnosing and monitoring of Alzheimer's disease and other diseases related to β-amyloid plaque deposition, such as Down's syndrome. Suitable patient samples include CSF, blood, serum, plasma, urine, tissue, and the like. Presence of the disease will generally be associated with elevated levels of ATF-βAPP, or elevated ratios of the amount of ATF-βAPP to the amounts of other secreted βAPP fragments (i.e., those βAPP fragments cleaved within or carboxy terminal to the βAP region) when compared to those values in normal individuals, i.e., individuals not suffering from Alzheimer's disease or other β-amyloid-related disease. The amount of ATF-βAPP may be compared to the amount of another species of APP, either an isoform (e.g., 695, 751 or 770) and/or a form further defined by its carboxy terminus (e.g., forms cut at and/or carboxy terminal to that site described by Esch et al.). In addition to initial diagnostic procedures, levels of ATF-βAPP may be monitored in order to follow the progress of the disease, and potentially follow the effectiveness of treatment. It would be expected that levels of ATF-βAPP would decrease with an effective treatment regimen.

In vitro monitoring of ATF-βAPP levels in cultured medium from a suitable cell culture may be used for drug screening. By growing cells under conditions which result in the secretion of ATF-βAPP into the culture medium, and exposing the cells to test compounds, the effect of these test compounds on ATF-βAPP secretion may be observed. It would be expected that test compounds which are able to diminish the amount of ATF-βAPP would be candidates for testing as inhibitors of βAP formation. Suitable cell lines include human and animal cell lines, such as 293 human kidney cell line, human neuroglioma cell lines, human HeLa cells, primary endothelial cells (e.g., HUVEC cells), primary human fibroblasts or lymphoblasts (including endogenous cells derived from patients with βAPP mutations), primary human mixed brain cells (including neurons, astrocytes and neuroglia), Chinese hamster ovary (CHO) cells, and the like. Cell lines which preferentially increase the levels or ratios of ATF-βAPP would be particularly useful in the methods of invention.

Similarly, in vitro monitoring of ATF-βAPP in animal models of Alzheimer's disease, such as the mouse model disclosed in WO 91/19810, the disclosure of which is incorporated herein by reference, may also be used to screen test compounds for therapeutic effectiveness (usually for testing of compounds which have previously been identified by an in vitro screen). The test compound(s) are administered to the animal and the level of ATF-βAPP or ratio of ATF-βAPP to other βAPP fragments observed. Those compounds which reduce the level of ATF-βAPP, or decrease the ratio of ATF-βAPP to other βAPP fragments, will be considered to be candidates for further evaluation.

Particularly preferred animal models for β-secretase cleavage of βAPP are transgenic animals which express the Swedish mutation of the βAPP gene, as described above. It has been found that such transgenic animals, particularly transgenic mice, produce high quantities of ATF-βAPP which may detected according to the methods of the present invention. In particular, it has been found that Swedish mutation of βAPP produces quantities of the ATF-βAPP which will usually be at least two-fold higher than wild type human βAPP expressed in animals. Usually, production will be significantly higher, typically being at least two-fold higher. With such elevated levels of ATF-βAPP production, monitoring β-secretase activity under different conditions is greatly facilitated. In particular, screening for drugs and other therapies for inhibiting β-secretase activity (and thus inhibiting βAPP production) are greatly simplified in animals models expressing the Swedish mutation of human βAPP.

The use of animal models for screening drugs for β-secretase inhibition activity will often be performed after in vitro cell culture screening techniques, as described above, have been performed. Drugs which appear promising in in vitro screening may then be administered to test animals, such as test mice, which are transgenic and which express the Swedish mutation of human βAPP. Particular techniques for producing transgenic mice which express the Swedish form of βAPP are described in the Experimental section hereinafter. It will be appreciated that the preparation of other transgenic animals expressing the Swedish human βAPP may easily be accomplished, including rats, hamsters, guinea pigs, rabbits, and the like.

The effect of test compounds on ATF-βAPP production in test animals may be measured in various specimens from the test animals. In the Experimental section, the detection of ATF-βAPP in brain homogenates is described in detail. Detection of ATF-βAPP in brain homogenates is exemplary, but not necessarily preferred. In some cases, it will be advantageous to measure the ATF-βAPP in other specimens, such as cerebrospinal fluid, blood, and the like, which may be obtained from the test animal without sacrifice of the animal.

In all cases, it will be necessary to obtain a control value which is characteristic of the level of ATF-βAPP production in the test animal in the absence of test compound(s). In cases where the animal is sacrificed, it will be necessary to base such control values on an average or a typical value from other test animals which have been transgenically modified to express the Swedish mutant of human βAPP but which have not received the administration of any test compounds or any other substances expected to affect the level of production of ATF-βAPP. Once such control level is determined, test compounds can be administered to additional test animals, where deviation from the average control value indicates that the test compound had an effect on the β-secretase activity in the animal. Test substances which are considered positive, i.e., likely to be beneficial in the treatment of Alzheimer's disease or other β-amyloid-related conditions, will be those which are able to reduce the level of ATF-βAPP production, preferably by at least 20%, more preferably by at least 50%, and most preferably by at least 80%.

The test compounds can be any molecule, compound, or other substance which can be added to the cell culture or administered to the test animal without substantially interfering with cell or animal viability. Suitable test compounds may be small molecules, biological polymers, such as polypeptides, polysaccharides, polynucleotides, and the like. The test compounds will typically be administered to the culture-medium at a concentration in the range from about 1 nM to 1 mM, usually from about 10 µM to 1 mM. The test compounds will typically be administered at a dosage of from 1 ng/kg to 10 mg/kg, usually from 10 µg/kg to 1 mg/kg.

Test compounds which are able to inhibit secretion or animal production of ATF-βAPP are considered as candidates for further determinations of the ability to block β-amyloid production in animals and humans. Inhibition of secretion or production indicates that cleavage of βAPP at the amino-terminus of βAP has likely been at least partly blocked, reducing the amount of a processing intermediate available for conversion to β-amyloid peptide.

The present invention further comprises methods for inhibiting β-amyloid production in cells, where the method includes administering to the cells compounds selected by the method described above. The compounds may be added to cell culture in order to inhibit βAP production by the cultured cells. The compounds may also be administered to a patient in order to inhibit the deposition of amyloid plaque associated with Alzheimer's and other βAP-related diseases.

The present invention further comprises pharmaceutical compositions incorporating a compound selected by the above-described method and including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Penn., 16th Ed., 1982, the disclosure of which is incorporated herein by reference.

The pharmaceutical compositions just described are suitable for systemic administration to the host, including both parenteral, topical, and oral administration. The pharmaceutical compositions may be administered parenterally, i.e. subcutaneously, intramuscularly, or intravenously. Thus, the present invention provides compositions for administration to a host, where the compositions comprise a pharmaceutically acceptable solution of the identified compound in an acceptable carrier, as described above.

Frequently, it will be desirable or necessary to introduce the pharmaceutical compositions directly or indirectly to the brain. Direct techniques usually involve placement of a drug delivery catheter into the host's ventricular system to bypass the blood-brain barrier. Indirect techniques, which are generally preferred, involve formulating the compositions to provide for drug latentiation by the conversion of hydrophilic drugs into lipid-soluble drugs. Latentiation is generally achieved through blocking of the hydroxyl, carboxyl, and primary amine groups present on the drug to render the drug more lipid-soluble and amenable to transportation across the blood-brain barrier. Alternatively, the delivery of hydrophilic drugs can be enhanced by intra-arterial infusion of hypertonic solutions which can transiently open the blood-brain barrier.

The concentration of the compound in the pharmaceutical carrier may vary widely, i.e. from less than about 0.1% by weight of the pharmaceutical composition to about 20% by weight, or greater. Typical pharmaceutical composition for intramuscular injection would be made up to contain, for example, one to four ml of sterile buffered water and one μg to one mg of the compound identified by the method of the present invention. The typical composition for intravenous infusion could be made up to contain 100 to 500 ml of sterile Ringer's solution and about 1 to 100 mg of the compound.

The pharmaceutical compositions of the present invention can be administered for prophylactic and/or therapeutic treatment of diseases related to the deposition of βAP, such as Alzheimer's disease and Down's syndrome. In therapeutic applications, the pharmaceutical compositions are administered to a host already suffering from the disease. The pharmaceutical compositions will be administered in an amount sufficient to inhibit further deposition of βAP plaque. An amount adequate to accomplish this is defined as a "therapeutically effective dose." Such effective dose will depend on the extent of the disease, the size of the host, and the like, but will generally range from about 0.01 μg to 10 mg of the compound per kilogram of body weight of the host, with dosages of 0.1 μg to 1 mg/kg being more commonly employed.

For prophylactic applications, the pharmaceutical compositions of the present invention are administered to a host susceptible to the βAP disease, but not already suffering from such disease. Such hosts may be identified by genetic screening and clinical analysis, as described in the medical literature. The pharmaceutical compositions will be able to inhibit or prevent deposition of the βAP plaque at a very early stage, preferably preventing even the initial stages of the β-amyloid disease. The amount of the compound required for such prophylactic treatment, referred to as a prophylactically-effective dosage, are generally the same as described above for therapeutic treatment.

The following examples are offered by way of illustration, not by way of limitation.

EXPERIMENTAL

Materials and Methods

1. Antibody and Affinity Matrix Preparation

Monoclonal antibody 6C6 was raised and screened in the same manner as antibody 10D5 (Hyman et al. (1992) J. Neuropath. Exp. Neurol. 51:76) using a synthetic peptide containing βAP residues 1–28 conjugated to rabbit serum albumin as the immunogen. Both 10D5 and 6C6 recognize an epitope within the first 16 amino acids of the βAP sequence. 6C6 was more efficient than 10D5 in immunoprecipitation and was used as a capture antibody. To prepare 6C6 resin, 4 mls of Affigel® 10 (Bio-Rad Laboratories, Hercules, Calif.) was washed with cold water and combined with 3 mls of 6C6 (12.5 mg/ml in PBS (2.7 mM KCl, 1.5 mM $KH_2PO_4$, 8.1 mM $Na_2HPO_4$, 137 mM NaCl, pH 7.5) 0.5M NaCl. The coupling proceeded overnight at 4° C. with gentle shaking. 400 μl of 1M Tris, pH 8.0, was then added, and shaking was continued for 40 minutes. The resin was then washed with TTBS (137 mM NaCl, 5 mM KCl, 25 mM Tris, 0.5% Tween®20, pH 7.5) exhaustively before use. Antibody 7H5 is also described in Hyman et al. (1992), supra. Anti-5 antibodies were raised against βAPP 444–592 (Oldersdorf et al. (1989) supra, and (1990) supra.

Antibodies (designated antibody 92) were raised against a synthetic peptide including residues 591–596 of βAPP (as numbered in Kang et al. (1987), supra). The peptide (N-acetyl-CISEVKM) was conjugated to rabbit serum albumin which had been activated with sulfo-maleimido benzoyl-N-hydroxysuccinimide ester to form an immunogen. Antisera were raised against the immunogen in rabbits by standard methodologies. During each inoculation, rabbits received 5 μg of immunogen in 0.1 ml injections subcutaneously at approximately 10 sites (50 μg/boost). The same peptide was coupled to Sulfo-link™ gel (Pierce Chemical Co., Rockford, Ill.) for the affinity purification of antibodies from the IgG fraction.

A more detailed description of the antibody 92 preparation is as follows. Rabbit serum albumin (12.3 mg) was incubated with 13 mg of sulfo-maleimido benzoyl-N-hydroxysuccinimide ester in 1.25 mls of 0.05M $KH_2PO_4$, pH 7.0 for 20 minutes at 0° C. The mixture was then immediately subjected to gel filtration on a 1×75 cm column of Sephadex G-10 equilibrated with the phosphate buffer. The protein eluant in the excluded volume was pooled and immediately combined with 30 mg of N-acetyl-CISEVKM peptide which was synthesized by standard automated solid phase methodologies. The coupling reaction (20 ml volume) was allowed to proceed overnight and was then sent to a commercial facility for antibody generation. The injection protocol was to emulsify the antigen in an equal volume of Freund's complete adjuvant and subcutaneously inject a total of 50 μg of antigen in 0.1 ml aliquots in approximately 10 sites. Every three weeks thereafter, a booster injection was given by an identical protocol except Freund's incomplete adjuvant was used as the emulsifier. Rabbits were bled one week following each injection and the serum examined for titer by reaction to peptide in ELISA. The IgG was purified from the positive reacting sera by precipitation with 50% $(NH_4)_2SO_4$, (2 x's) and dialyzed against PBS. The N-acetyl-CISEVKM peptide was conjugated to Sulfo-link™ gel (Pierce Chemical Co., Rockford, Ill.) using the manufacturer's recommendations to generate an affinity resin to purify the peptide specific antibodies. The IgG fraction was applied to the column and, after washing through non-specifically bound material with PBS, the antibodies were eluted with 0.1M glycine pH 2.5 0.5M NaCl and then dialyzed vs PBS before freezing.

Swedish 192 antibody was raised against a synthetic peptide composed of residues 590–596 of the Swedish βAPP sequence. In addition to the βAPP sequence, two glycines and a cysteine were added as a spacer and a linker giving the following sequence: CGGEISEVNL. The peptide was conjugated to a commercially available maleimide activated cationized Bovine Serum Albumin (Pierce Imject Supercarrier Immune Modulator, hereafter referred to as cBSA.) Antiserum was raised by following the injection schedule described above for antibody 92.

In general, cBSA was resuspended in deionized water to a concentration of 10 mg/ml. An equal milligram amount of peptide was added to the carrier and mixed for four hours at room temperature. The conjugate was then dialyzed extensively against Dulbecco's phosphate buffered saline without calcium and magnesium.

The conjugate was compared to the starting cSSA on a 6% Novex pre-poured Tris-glycine gel. Successful conjugation was indicated by a visible shift to a higher molecular weight.

2. Human Fetal Brain Cell Culture

Fetal neural tissue specimens were obtained from 12–14 week old fetal cadavers. Samples of cerebral cortex were rinsed twice with Hank's Balanced Saline Solution (HBSS). Cortical tissue (2–3 grams) was placed in 10 mls of cold HBSS to which 1 mg of DNase (Sigma Chemical Co., St. Louis, Mo. D3427) was added. The triturated suspension was filtered through Nitex nylon screens of 210 μm the 130 μm, as described by Pulliam et al. (1984) J. Virol. Met. 9:301.

Cells were harvested by centrifugation and resuspended in neuronal medium (MEM fortified with 10% fetal bovine serum, 1% glucose, 1 mM NaPyruate, 1 mM glutamine, 20 mM KCl). Polyethyleneimine coated 100 mm dishes were seeded with $1.5 \times 10^7$ cells in 8 mls of neuronal medium. The medium was exchanged twice weekly. All cultures in this study were grown in vitro at least 30 days. For serum-free growth conditions, cultures were shifted into defined medium (DMEM supplemented with 5 μg/ml bovine insulin; 0.1 mg/ml human transferrin; 0.1 mg/ml BSA fraction V; 0.062 μg/ml progesterone, 1.6 μg/ml putrescine; 0.039 μg/ml sodium selenite, 0.042 μg/ml thyroxine; and 0.033 μg/ml triiodo-L-thyronine), and after 3 days the supernatant was harvested.

Conditioned medium from the cells (10 ml) was harvested. EDTA (5 mM), leupeptin (10 μg/ml), and Tris-HCl (20 mM, pH 8.0) were added to each 10 ml sample at the indicated final concentration, and the sample spun 30,000 xg for 20 minutes at 4° C. The resulting supernatant was divided into two equal aliquots, 6C6 resin was added to one of the aliquots (200 μl of resin with approximately 5 mg/ml 6C6 bound). Both aliquots were gently mixed for 6 hours at 4° C, the resin was pelleted, and a second 200 μl aliquot of resin was added. The samples were further mixed overnight at 4° C. The combined resins were washed twice with TTBS, then briefly extracted twice with one ml aliquots of 0.1M glycine, 0.1M NaCl, pH 2.8.

The material extracted from the resin, the medium depleted by the resin, and the starting medium were individually precipitated with 10% TCA (trichloro-acetic acid) at 0° C. for one hour, the pellets washed with acetone and then resuspended in 150 μl of SDS-PAGE sample buffer under reducing conditions and boiled. Each sample (25 μl) was subjected to SDS-PAGE using 10–20% tricine gels (Novex). The proteins were transferred to ProBlot PVDF membranes overnight at 40 V. Visualization of immunoreactive proteins employed the TROPIX chemiluminescence system according to the manufacturer's directions for the AMPPD substrate. Primary antibody concentrations used were: anti-5, 0.1 μg/ml; 92, 2 μg/ml; 10D5, 2 μg/ml.

3. Culture of Human 293 Cells

Human 293 cells (ATCC No. CRL-1573) were modified to overexpress APP (Selkoe et al. (1988) Proc. Natl. Acad. Sci. USA 85:7341). Cells were grown in 10 cm dishes to subconfluency prior to use. Metabolic labelling and immunoprecipitation were performed essentially as previously described in Oltersdorf et al. (1989) Nature 341:144 and (1990) J. Biol. Chem. 265:4492. In brief, labelling was performed in 10 cm dishes. Cells were washed in methionine-free medium, incubated for 20 minutes in 2 ml methionine-free medium supplemented with 0.5 mCi $^{35}S$-methionine, washed in full medium, and chased for 2 hours in 3 ml of full medium. Conditioned medium was collected and cleared at 3000 xg for 10 minutes followed by preabsorption with protein A Sepharose® (Pharmacia, Piscataway, N.J.). Immunoprecipitation was performed with 1.5 mg protein A Sepharose® per sample. Antibody anti-5 was used at 2 μg per sample; 6C6, 7H5 and 92 were used at 10 μg per sample. 5 mg of rabbit anti mouse IgG were used with 6C6 and 7H5 as well as in the control samples. Precipitates were washed four times in TBS (137 mM NaCl, 5 mM KCl, 25 mM Tris, pH 7.5), 0.1% NP40, 5 mM EDTA, 1 mM PMSF, 10 μg/ml leupeptin. SDS-PAGE was performed on 5% Laemmli gels.

4. Culture of Human 293 Cells Transfected with Swedish Mutation.

Duplicate wells in a 6 well tray of human kidney 293 cells were transiently transfected with plasmid vectors expressing either normal human βAPP or the Swedish mutation variant βAPP using DOTAP mediated transfection as described by the manufacturer (Boehringer Mannheim). 40 hours later the cells were placed into methionine free DME containing 10% fetal calf serum and 20 minutes later they were labeled for 35 minutes with 200 μCi/ml $^{35}S$-methionine. The cells were then placed back into normal DME medium containing 10% fetal calf serum and incubated another 2.5 hours. The medium was collected from the cells, and spun at 1000 xg for 15 minutes to remove all the cells. The supernatants were split in half and half was immunoprecipitated with anti-5 antibody by standard methods. The other half was incubated overnight with agarose-coupled 6C6 antibody, and the material bound to the 6C6 agarose was separated by centrifugation. The remaining material was then immunoprecipitated with anti-5 antibody. The total anti-5 immunoprecipitates (α5+), 6C6 bound precipitates (6C6+) and 6C6 non-reactive, anti-5 reactive immunoprecipitates (6C6-,α5+) were run on a 5% Laemmli gel and immunoreactive proteins were visualized by autoradiography.

5. Specificity of the Swedish 192 antibody.

Conditioned medium from 293 kidney cells, which have been stably transfected to overexpress the Swedish βAPP protein, was collected. One milliliter aliquots were added to either 100 μl of immobilized 6C6-affinity resin (see above) or 100 μl of heparin agarose (Sigma). The reaction with the 6C6 resin was for 5 hours at 4° C.; the heparin-agarose was reacted for 30 minutes at 4° C. After incubation, the resins were washed with TTBS and then 100 μl of 2×SDS-PAGE sample buffer were added to each sample, the samples were boiled (5 minutes) and briefly centrifuged. Twenty μl of the samples were loaded onto 6% SDS-polyacrylamide gels and electrophoresed. The proteins were transferred to ProBlot® membranes as described above. The samples were probed with the following antibodies: 6C6 (described above), Swedish 192 (see above), or 8E5 (a monoclonal antibody which recognizes an epitope of βAPP in the region of amino acids 444–592, using the numbering of the 695 form.) All antibodies were used at 2 μg/ml during the probing of the immunoblot. The visualization of immunoreactive material was achieved using the Amersham ECL® system according to the manufacturer's recommendations. Blocking and antibody dilutions were made using 5% non-fat dry milk (Carnation) in TTBS.

6. Transgenic Mice.

Transgenic mice were generated using the plasmids shown in FIG. 7 (NSEAPPsw and NSEAPPswΔ3'). These plasmids contain the 751 form of βAPP containing the Swedish mutation (KM to NL at position 595 and 596 of the 695 form). The neural specific enolase promoter drives expression and provides a splice sequence. The rat NSE promoter and splice sequences were derived from pNSE6 (Okayama and Berg (1982) Mol. Cell. Biol. 2:161–170. This vector contains the 4.2 kb BglII fragment of the rat NSE promoter region (starting from the upstream BglIIsite and continuing to the BglII site in the second intron) cloned into the BamHI site of the vector pSP65 (Promega). The vector-derived XbaI site at the 5' end of the promoter defined the 5' end of the promoter used and the NSE translation initiating ATG, contained within the second intron, was fused to the βAPP-initiating ATG.

NSEAPPsw also contains a splice sequence from SV40 in the 3' region of the gene. This splice sequence was derived from the Okayama/Berg vector pL1, and is a fusion of the late 16s and 19s message splice sequences (Forss-Petter et al. (1990) Neuron 5:187–197). Polyadenylation is provided by SV40 sequences.

Transgenic mice incorporating these plasmid sequences were generated using standard techniques. The NotI fragment containing the above described expression cassette was purified and injected into eggs obtained from a C57Bl/DBA hybrid mouse. The eggs were implanted into pseudopregnant mice and the offspring were screened for presence of plasmid sequences in tail DNA by PCR, slot blot and Southern analysis. The founder mice thus generated were screened for expression of human βAPP by analysis of their F1 transgenic offspring. Brains from the F1 animals were homogenized with a hand held homogenizer (polytron PT122B, Kinematica AG) either in SDS buffer (2% SDS, 20 mM Tris pH 8.0, 150 mM NaCl, 10 mM EDTA) or homogenized in NP-40 buffer (1% NP40, 50 mM Tris pH 7.5, 10 mM EDTA, and a cocktail of protease inhibitors containing 5–10 μg/ml leupeptin, 2–4 μg/ml Pepstatin A, 5–10 μg/ml Aprotinin, and 1–2 mM PMSF). The SDS lysates were loaded directly onto gels for Western analysis. The NP40 homogenates were spun at 55,000 rpm for 10 minutes in a Beckman ultracentrifuge (T1100.3 rotor) and the supernatants were loaded onto gels for Western analysis. The Western analysis was done by standard procedures utilizing either anti-5 (0.4 μg/ml) or 8E5 (5 μg/ml) antibodies to detect the human specific βAPP. Those lines expressing relatively high levels of βAPP were chosen for further analysis. This included the lines Hillary 14, Chelsea 32 and Chelsea 58. The experiments described here were done on heterozygote animals of these lines derived by breeding transgene containing animals with wild type animals and screening the offspring for presence of the transgene. Similarly, homozygous animals from a selected number of lines can be used.

Description of the Experimental Figures

FIG. 2: Demonstration of Truncated βAPP in Conditioned Medium from Human Mixed-Brain Cell Cultures.

Sample 1 is the conditioned-medium from culture; sample 2 is the medium depleted of 6C6-reactive βAPP; and sample 3 is the material extracted from the 6C6 resin. Panel A was probed with anti-5 antibodies which were raised against the βAPP sequence 444–592 (Oltersdorf et al. (1989) supra, and (1990) supra. Panel B was probed with antibody 92, described in the Materials and Methods section. Panel C was probed with 10D5, a monoclonal antibody which recognizes an epitope within βAP residues 1–16, as described in the Materials and Methods section. The lower molecular weight bands observed in C2 and C3 were not seen in C1 and are derived from the 6C6 resin and are recognized by goat-anti-mouse IgG alkaline phosphatase conjugate independent of a primary antibody (data not shown).

Figure 3:
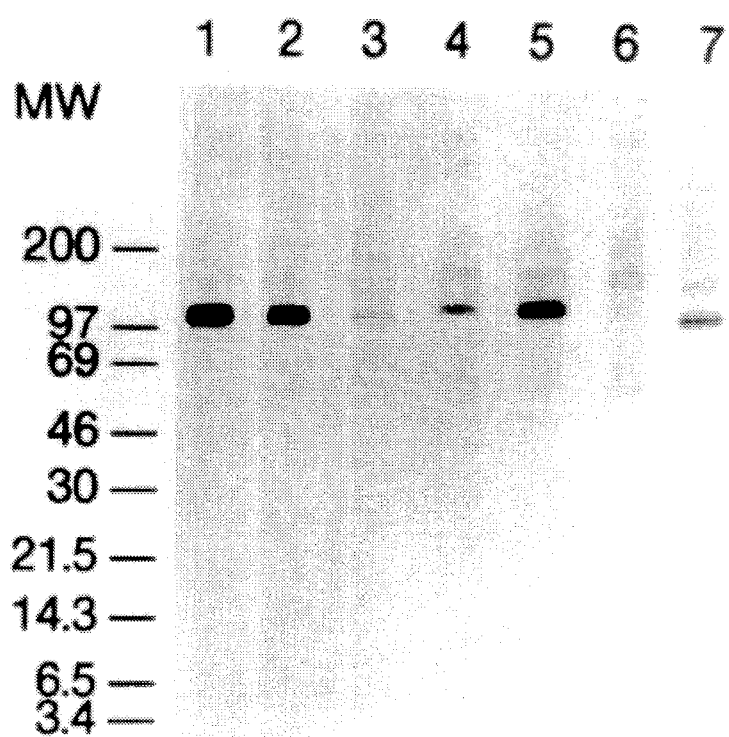
FIG. 3 is a chemiluminescent gel pattern obtained by examining human lumbar CSF. The CSF was probed with 92 antibody either alone (lane 1) or preincubated with various peptides representing variations of the C-terminus of ATF-βAPP. A significant competition (reduction in binding) was observed with peptides terminating in the C-terminal methionine (lanes 3, 4, 6, and 7). The peptides were as follows: Lane 1, no competing peptide added; Lane 2, GSGLTNIKTEEISEVK; Lane 3, YSGLTNIK-TEEISEVKM; Lane 4, ISEVKM; Lane 5, EISEVKMD; Lane 6, CISEVKM; Lane 7, YISEVKM. MW=molecular mass markers (indicated in kilodaltons).

FIG. 3: Specificity of 92 Antibodies.

One milliliter of a human lumbar CSF specimen obtained from a 75 year old male was precipitated with 10% TCA to effect a ten-fold concentration and processed as described in FIG. 2, except that the gel well was a 4 cm slot. The 92 antibody was diluted to 6.7 μg/ml in 0.5 mls of TTBS in the presence of various potentially competing peptides, each at an approximate concentration of 60 μM, for 10 hours at 4° C. with gentle mixing. The antibody was then diluted eight-fold in 1% gelatin/TTBS before incubation with strips of the blot of CSF-derived material and processed as described in FIG. 2. The competing peptides were as follows: Lane 1, no competing peptide added; Lane 2, GSGLT-NIKTEEISEVK; Lane 3, YSGLTNIKTEEISEVKM; Lane 4, ISEVKM; Lane 5, EISEVKMD; Lane 6, CISEVKM; Lane 7, YISEVKM. MW=molecular mass markers (indicated in kilodaltons).

Figure 4:
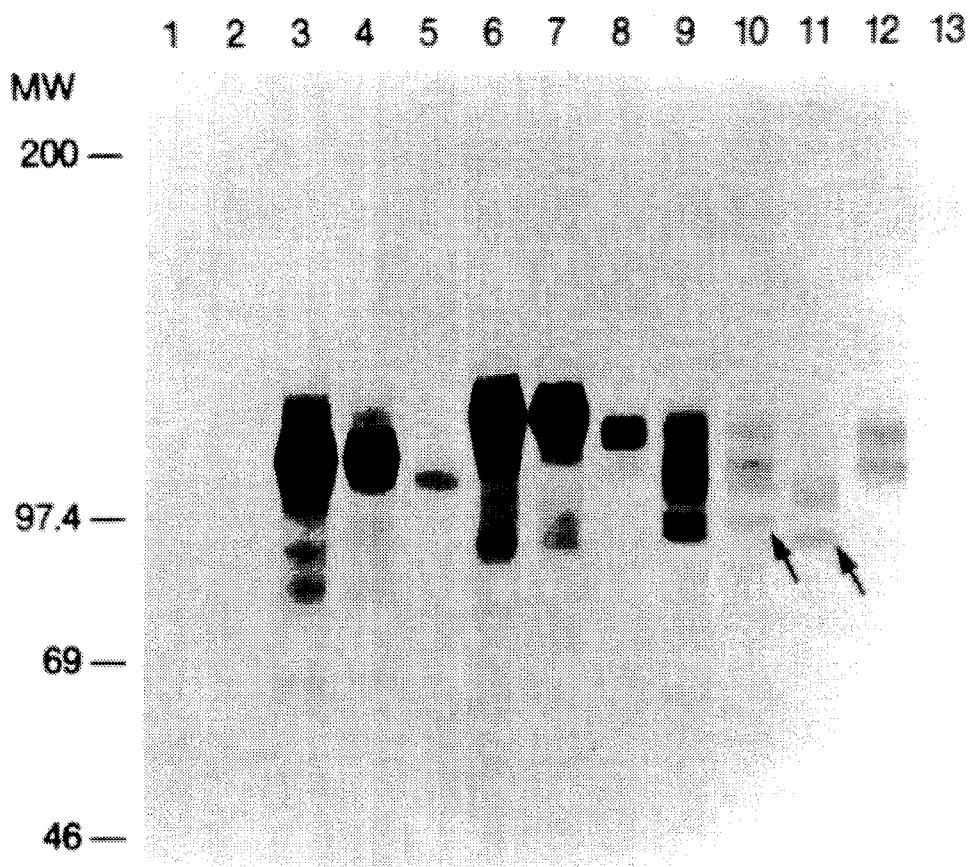
FIG. 4 is an autoradiogram representing electrophoretic gel patterns obtained by immunoprecipitation of conditioned medium from various cell lines. The material secreted by human fetal brain cultures and immunoprecipitated by antibody 92 (lane 11 at the arrow) is apparently smaller than the material precipitated by antibody 6C6 (lane 10 at the arrow). Antibody 6C6 recognizes an epitope within residues 116 of βAP.

FIG. 4: Molecular mass heterogeneity of secreted forms of APP in immunoprecipitation detected by antibodies against different C-termini in cell lines and primary human fetal brain cultures.

Antibodies: anti-5: Lanes 3, 6, 9; 6C6 (directed against βAP peptide residues 1–16): Lanes 4, 7, 10; antibody 92 (against APP amino acids 591 to 596): Lanes 5, 8, 11; 7H5 (against APP-KPI): Lane 12. Cells: left panel (lanes 1 and 35): 293 cells stably transfected with APP 695; middle panel (lanes 2 and 6–8): 293 cells stably transfected with APP 751; right panel (lanes 9–13): human fetal brain cultures. Controls: lanes 1, 2, and 13: rabbit anti mouse IgG antibody. Arrows: an example of molecular mass difference between secreted forms of APP recognized by antibodies 6C6 and 92. SDS-PAGE was performed on a 5% Laemmli gel. MW=molecular mass markers (indicated in kilodaltons).

Figure 5:
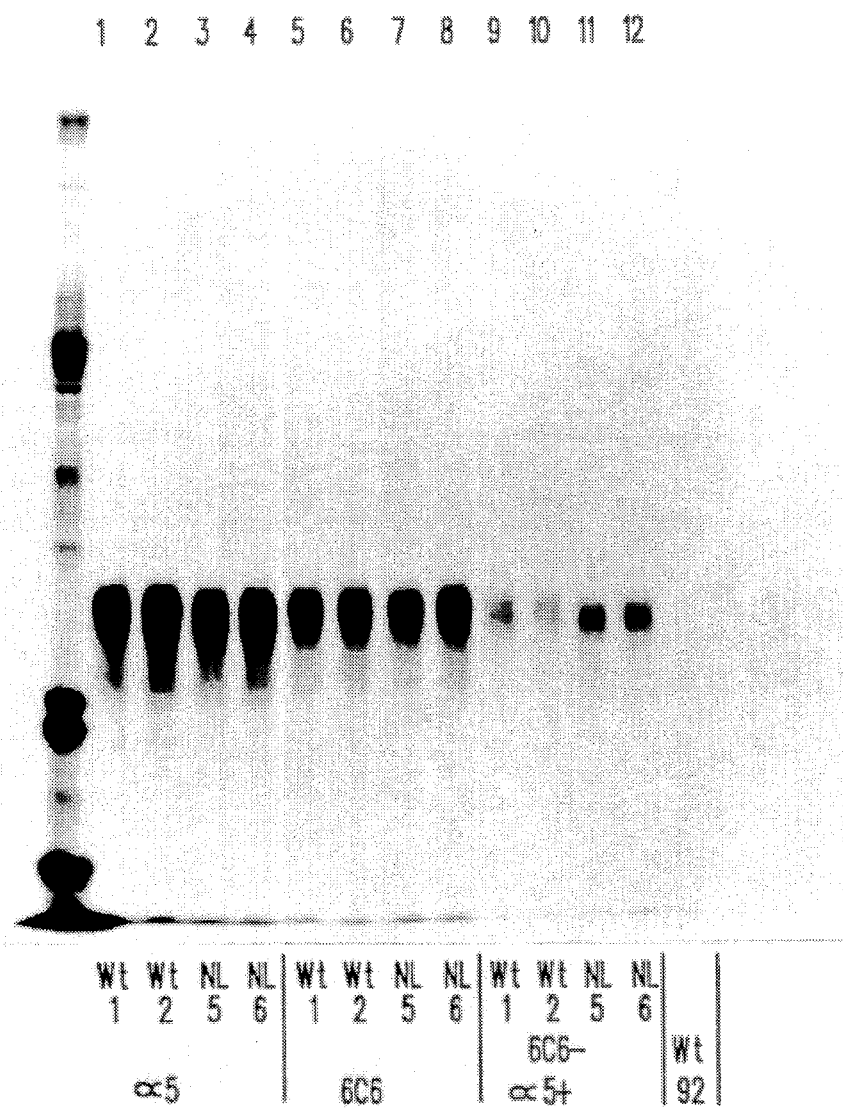
FIG. 5 is an autoradiogram representing electrophoretic gel patterns obtained by immunoprecipitation of conditioned medium from human 293 cell lines transfected with cDNA encoding both normal and Swedish βAPP. The amount of AFT-βAPP material secreted by the Swedish transfected cells (lanes 11 and 12) is qualitatively greater than that produced by normal βAPP transfectants (lanes 9 and 10).

FIG. 5: Demonstration of truncated βAPP in conditioned medium from human 293 cells transfected with Swedish mutation.

FIG. 5 shows results from duplicate transfections for both normal and Swedish forms. Lanes 1–4 are α5+; lanes 5–8 are 6C6+; and lanes 9–12 are 6C6-, α5+ samples. Lanes 1, 2, 5, 6, 9 and 10 are from normal βAPP, lanes 3, 4, 7, 8, 11 and 12 are from Swedish βAPP. The Swedish mutation results in the production of increased AFT-βAPP as lanes 11 and 12 contain more ATF-βAPP material than lanes 9 and 10.

Figure 6:
FIG. 6 is an immunoblot demonstrating specificity of a monoclonal antibody raised against the Swedish mutation of ATF-βAPP (referred to hereinafter as the Swedish 192 antibody).

FIG. 6: Immunoblot demonstrating specificity of the Swedish 192 antibody.

FIG. 6 shows an immunoblot demonstrating specificity of the Swedish 192 antibody. Lanes 1, 3, 5 contain material eluted from heparin agarose. Lanes 2, 4, 6 contain material eluted from the 6C6 resin. Lanes 1 and 2 were probed with antibody 8E5; Lanes 3 and 4 were probed with the Swedish 192 antibody; Lanes 5 and 6 were probed with antibody 6C6.

Figure 7A:
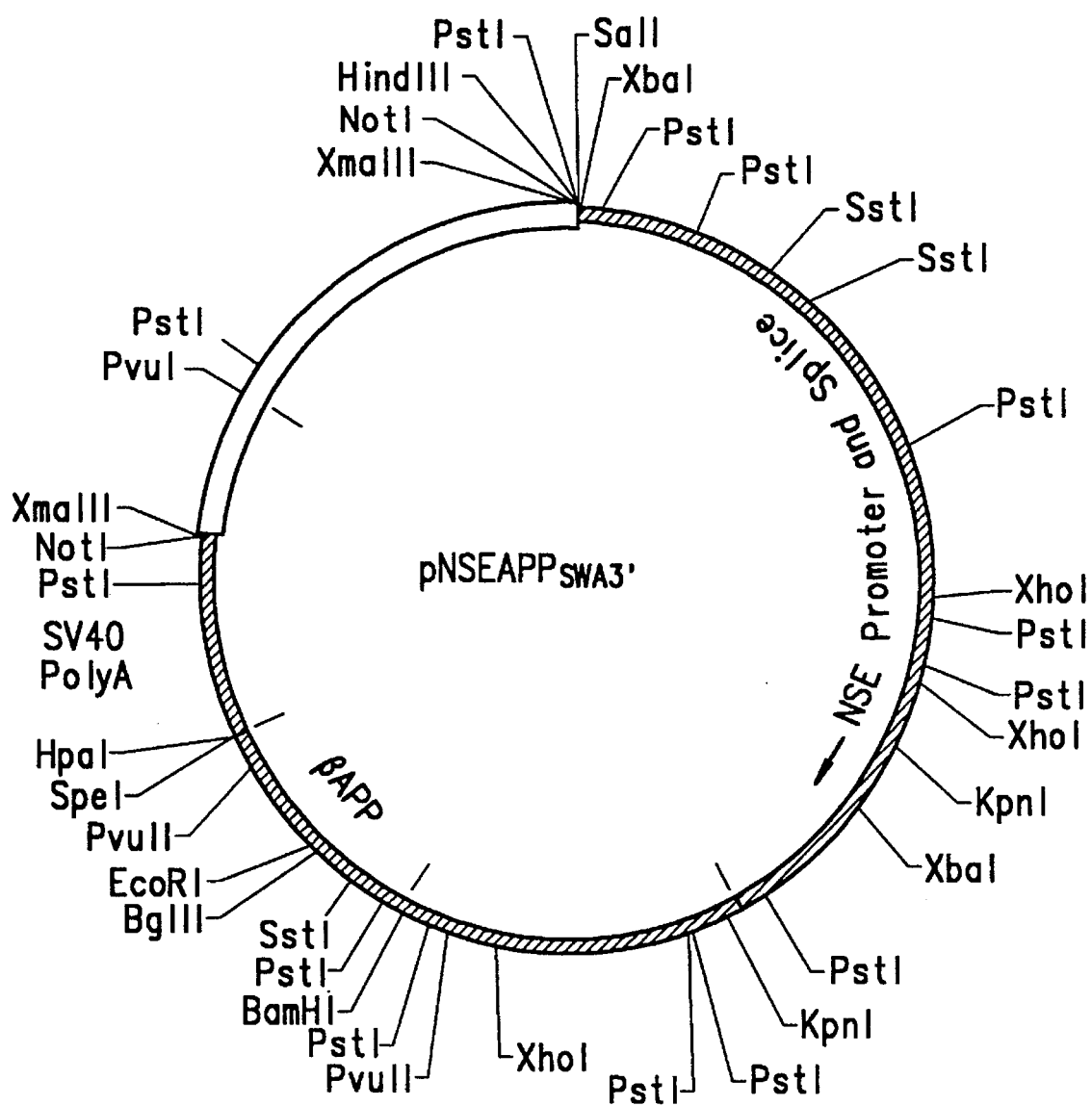
FIG. 7A is a map of plasmid pNSEAPPswΔ3'.
Figure 7B:
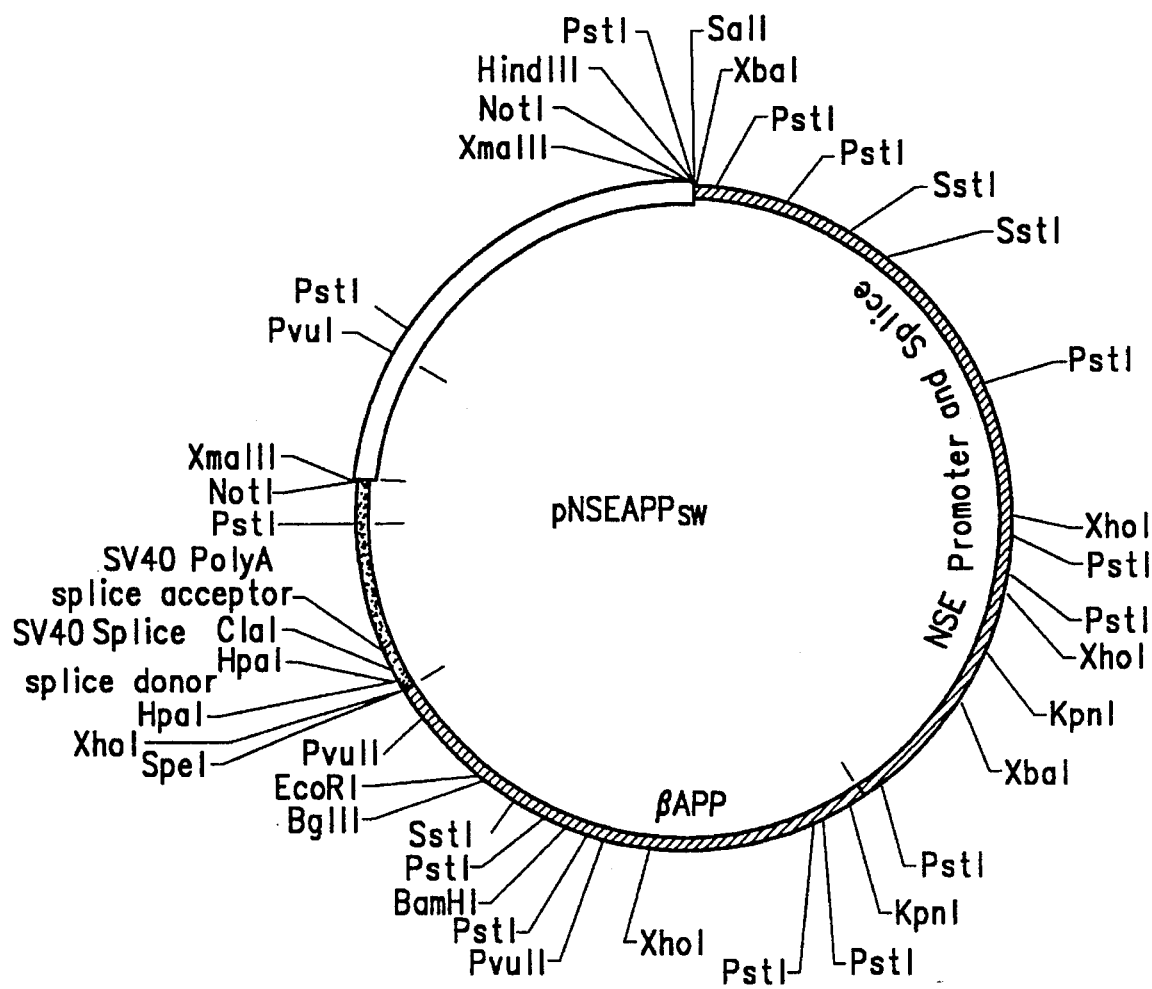
FIG. 7B is a map of plasmid pNSEAPPsw.

FIGS. 7A and 7B: Plasmid Maps.

FIGS. 7A and 7B are plasmid maps of pNSEAPPswΔ3' and pNSEAPPsw, respectively, which are used to produce transgenic mice as described above.

Figure 8:
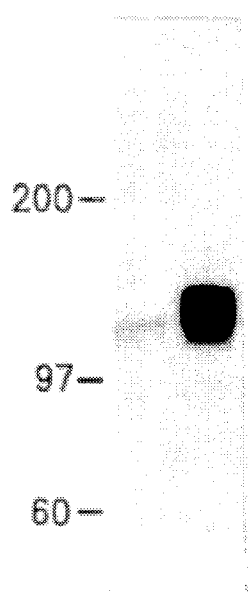
FIG. 8 is a Western blot of soluble fractions of transgenic and non-transgenic (control) mice brain homogenates probed for the presence of βAPP fragments.

FIG. 8: Western Blot

FIG. 8 is a Western blot of soluble fractions of transgenic and control animal brains probed for the presence of secreted βAPP fragments reactive with the Swedish 192 antibody. Lane 1: molecular weight markers; lane 2: non-transgenic line; lane 3: transgenic line.

FIG. 9: Western Blot.

Figure 9A:
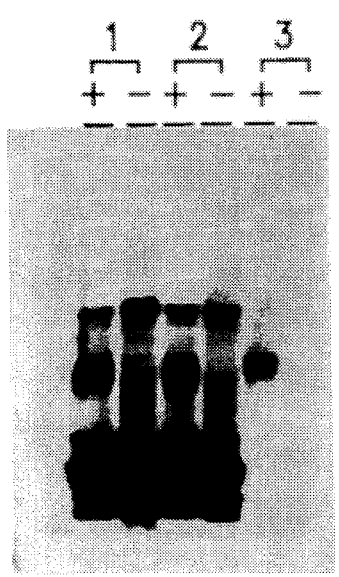
FIG. 9 are Western blots of brain homogenates from transgenic and non-transgenic (control) mice demonstrating that the Swedish 192 antibody does not cross-react with fragments of βAPP cleaved at the α-secretase site.
Figure 9B:
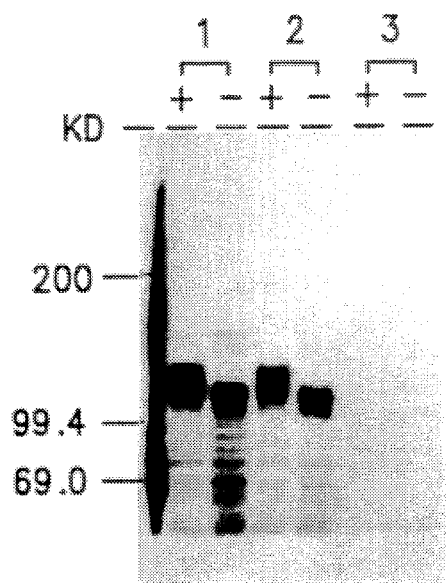

FIGS. 9A and 9B are Western blots of brain homogenates from transgenic (+) and non-transgenic (−) animals depleted of 6C6 antibody-reactive βAPP forms probed with antibody 8E5 (panel A) and Swedish 192 antibody (panel B).

Results

Monoclonal antibody 6C6 which recognizes an epitope of βAP within residues 1–16 was used to immuno-deplete certain βAPP fragments from various samples. The monoclonal antibody 6C6 was coupled to resin (as described above) and incubated with the conditioned medium from human fetal brain cell cultures as described above. As can be seen (FIG. 2, lane C2), this resin effectively removes the βAPP containing βAP 1–6 from the conditioned medium of the cell culture. Substantial βAPP immunoreactivity, however, is not captured by the resin as detected by anti-5 antibody directed against an epitope N-terminal to the βAP region (FIG. 2, lane A2).

In order to characterize this apparently novel form of βAPP, we raised antibodies against a synthetic peptide which included βAPP residues 591–596 (as described above). This antibody (designated 92) was found to recognize the species of βAPP not captured by the resin, (FIG. 2, lane B2) but surprisingly did not react with the secreted form of βAPP containing the βAP 1–16 sequence (lane B3).

The explanation for this lack of cross reactivity appears to be that the 92 antibody recognizes an epitope in βAPP including the carboxy terminal methionine, corresponding to residue 596. Accordingly, we examined the ability of various synthetic peptides to block the immunoreactivity generated with 92. As can be seen in FIG. 3, βAPP sequence-based peptides ending with the equivalent of methionine 596 substantially block the reaction of 92, while peptides one amino acid longer or shorter at their carboxy termini are comparatively ineffective in competition. The same pattern of peptide competition was observed in cell culture supernatants (data not shown) and in CSF. A series of pulse-chase experiments revealed that detectable amounts of antibody 92 immunoprecipitable material are produced by 293 cells overexpressing either the 695 or 751 isoforms of βAPP (FIG. 4, lanes 5 and 8). Similar experiments on human fetal brain cell cultures show that 92 immunoprecipitable material can be resolved from 6C6 reactive βAPP by low percentage (5%) SDS-PAGE (FIG. 4, lanes 9–11). In the fetal brain cell cultures, the alternative processing of Kunitz protease inhibitory domain (KPI)-containing βAPP forms is less apparent, although faint co-migrating bands are observed with antibody 92 and anti-KPI antibody 7H5 immunoprecipitations (lanes 11, 12).

The ability to resolve the antibody 92 and 6C6 precipitable materials in mixed brain cultures is due, at least in part, to the nearly equal amounts of the respective forms produced as compared to the situation in 293 cells. Estus et al. (1992), supra, observed that compared with other tissues, human brain contained a relatively higher amount of the potentially amyloidogenic carboxy terminal fragment that, based upon size, appears to begin at or near the amino-terminus of βAP.

The temporal coincidence of the appearance of antibody 92 and 6C6 precipitable βAPP materials argues against the likelihood of a second proteolytic event occurring post-secretion, particularly since longer chase times do not result in a noticeable alteration in the ratio of the 92 and 6C6 reactive species (data not shown). The resolution of the secreted forms by SDS-PAGE, coupled with the complete lack of immunological cross-reactivity of these species, further demonstrate the existence of an alternative secretory pathway. The alternative cleavage site was designated as the β-secretase site to emphasize that cleavage occurs amino-terminal to the βAP as distinct from the cleavage described by Esch et al. (1990) supra which occurs within the βAP.

As can be seen in FIG. 6, lane 4, the Swedish 192 antibody does not appreciably recognize the 6C6 reactive form of βAPP despite the fact that more total βAPP is present in lane 4 compared to lane 3 (compare lanes 1 and 2.) The lack of reactivity with βAPP forms containing the partial βAP sequence (6C6-reactive) suggests the Swedish 192 antibody recognizes βAPP cleaved at or near the amino-terminus of βAP, but not when βAPP extends past this region.

In order to verify the utility this approach as an animal model, soluble fractions of transgenic animal brains were probed for the presence of the "92" form of the secreted βAPP (FIG. 8). This form is produced as a byproduct of the production of βAP and inhibition of the production of this form in cultured cells accompanies inhibition of the cleavage of the N-terminal end of βAP, the site cleaved by β-secretase.

Brains from transgenic (Swedish Hillary 14) or non-transgenic mice were homogenized in 50 mM Tris 10 mM EDTA together with the above described protease inhibitor cocktail and centrifuged at 55K rpm for 10 min as described above. The supernatant was analyzed by Western blot utilizing the Swedish "192" antibody that reacts only with the secreted form of βAPP produced by β-secretase. For Western analysis proteins were separated on a 6% SDS PAGE gel (from Novex) and then transferred to immobilonP by standard techniques. The filter was incubated with 2 µg/ml of the Swedish "192" antibody using standard techniques, and the bound antibody visualized using the AmershamECL kit. As shown in FIG. 8, lane 3, there was robustly detectable "192" reactive material in the supernatant from the transgenic animal. The non-transgenic animal brain homogenate contained a low amount immunoreactive material that is slightly faster in mobility on the gel than the material specific to the transgenic animal (lane 2). This material is probably not related to βAPP since it does not hybridize with other βAPP antibodies (e.g. anti-5).

In tissue culture systems, the Swedish 192 antibody does not cross-react with secreted βAPP that is cleaved at the β-secretase site at position 17 in the middle of the βAP sequence. To prove that this is also true in the mouse models, brain homogenates were depleted of the α-secretase-cleaved βAPP forms using resin bound to 6C6 antibody, which is specific for the first 16 amino acids of the βAP, and therefore reacts with amino-terminal fragment of the α-secretase cleaved secreted βAPP fragment but not with the shorter β-secretase cleaved secreted βAPP fragment. Resin was produced by using Actigel-ALS coupled in suspension as described by the manufacturer (Sterogene). An excess of resin-antibody was incubated with the brain homogenates from animals either containing or not containing the transgene for an initial incubation of 3 hours at 4° C. with shaking, and bound and unbound material was separated by centrifugation at 14,000 rpm for 1 min. The supernatant was again incubated with an excess of 6C6 coupled resin for 16 hours at 4° C. and again centrifuged to separate the unbound material. Material that bound during the first incubation and material that did not bind to the 6C6 coupled resin were analyzed by Western blot utilizing 8E5 and Swedish 192 antibodies (FIG. 9).

Homogenates from transgenic (+) or non-transgenic (−) mice were probed with 8E5 (panel A) or Swedish 192 (panel B). Lanes 1 refer to total homogenate, lanes 2 refer to the fraction that did not bind to the 6C6 resin (i.e., which is depleted of the α-secretase cleaved fragment of βAPP), and lanes 3 refer to the fraction that bound to the 6C6 coupled resin (i.e., which retains the α-secretase cleaved fragment of βAPP). None of the bound βAPP, identified by its reactivity to anti-5 antibody, cross-reacted with the Swedish 192 antibody. Unbound material, identified by reactivity to anti-5, reacted with the Swedish 192 antibody.

Thus, the present invention provides a viable animal model for elucidating the processing of βAPP into βAP and related fragments and further provides a convenient system for screening for inhibitors of β-secretase activity and/or for drugs that modulate β-secretase activity.

Although the foregoing invention has been described in detail for purposes of clarity of understanding, it will be obvious that certain modifications may be practiced within the scope of the appended claims.

What is claimed is:

1. A method for monitoring β-amyloid precursor protein (βAPP) processing in vivo, said method comprising specifically detecting the presence of Swedish variant amino terminal fragment of βAPP (ATF-βAPP) in a specimen from rodent transformed to express the Swedish mutation of human βAPP, wherein the amino terminal fragment has been cleaved between $Leu^{596}$ and $Asp^{597}$.

2. A method as in claim 1, wherein the presence of the ATF-βAPP is detected by reaction of the specimen with a binding substance specific for an epitope at the carboxy terminus of ATF-βAPP, said epitope comprising amino acids Ser-Glu-Val-Asn-Leu wherein Leu is a carboxy-terminal amino acid.

3. A method as in claim 2, wherein the binding substance is a monoclonal antibody raised against a peptide whose amino acid sequence is Ser-Glu-Val-Asn-Leu.

4. A method as in claim 1, wherein the specimen is selected from the group consisting of cerebrospinal fluid and brain homogenate.

5. A method as in claim 1, wherein the rodent is a mouse.

6. A method for determining whether a compound inhibits the production of β-amyloid peptide, said method comprising:
   administering a test compound to an a rodent transformed to express the Swedish mutation of human β-amyloid precursor protein (βAPP);
   specifically detecting the amount of Swedish variant amino terminal fragment of βAPP (ATF-βAPP) cleaved between $Leu^{596}$ and $Asp^{597}$ produced by the animal; and
   comparing the detected amount of Swedish variant ATFβ-APP with a control amount of Swedish variant ATF-βAPP produced in the absence of the test compound.

7. A method as in claim 6, wherein the presence of the ATF-βAPP is detected by reaction of the specimen with a binding substance specific for an epitope at the carboxy terminus of ATF-βAPP, said epitope comprising amino acids Ser-Glu-Val-Asn-Leu wherein Leu is a carboxy-terminal amino acid.

8. A method as in claim 7, wherein the binding substance is an antibody raised against a peptide whose amino acid sequence is Ser-Glu-Val-Asn-Leu.

9. A method as in claim 6, wherein the specimen is selected from the group consisting of cerebrospinal fluid and brain homogenate.

10. A method as in claim 6, wherein the rodent is a mouse.

11. A method as in claim 6, wherein the control amount of ATF-βAPP is measured in the same rodent which receives the test compound.

12. A method as in claim 6, wherein the control amount of ATF-βAPP is an average value determined from a plurality of test rodents expressing the Swedish mutation of human βAPP.

13. A method for detecting an amino-terminal fragment of the Swedish mutation of β-amyloid precursor protein (βAPP) in a biological specimen, said method comprising:
    exposing the specimen to a binding substance which binds specifically to an epitope at the carboxy terminus of ATF-βAPP, said epitope comprising amino acids Ser-Glu-Val-Asn-Leu wherein Leu is a carboxy-terminal amino acid; and
    detecting binding between the substance and the amino-terminal fragment.

14. A method as in claim 13, wherein the binding substance is an antibody.

15. A method as in claim 14, wherein the antibody has been raised against a peptide whose amino acid sequence is Ser-Glu-Val-Asn-Leu.

16. A method as in claim 15, wherein the antibody is a monoclonal antibody.

17. Antibodies specific for an epitope at the carboxy terminus of ATF-βAPP, said epitope comprising amino acids Ser-Glu-Val-Asn-Leu wherein Leu is a carboxyl-terminal amino acid.

18. Antibodies as in claim 17, raised against a peptide whose amino acid sequence is Ser-Glu-Val-Asn-Leu.

19. Antibodies as in claim 18, wherein the antibodies are monoclonal antibodies.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Gly Ser Gly Leu Thr Asn Ile Lys Thr Glu Glu Ile Ser Glu Val Lys
1               5                   10                  15

( 2 ) INFORMATION FOR SEQ ID NO:2:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Tyr Ser Gly Leu Thr Asn Ile Lys Thr Glu Glu Ile Ser Glu Val Lys
1               5                   10                  15

Met ( 2 ) INFORMATION FOR SEQ ID NO:3:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Ile Ser Glu Val Lys Met
1               5

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

Glu Ile Ser Glu Val Lys Met Asp
1               5

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

Cys Ile Ser Glu Val Lys Met
1               5

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

Tyr Ile Ser Glu Val Lys Met
1               5

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Asp Arg Gly Leu Thr
1               5

( 2 ) INFORMATION FOR SEQ ID NO:8:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:8:

Thr Arg Pro Gly Ser Gly Leu Thr Asn Ile
1               5                   10

(2) INFORMATION FOR SEQ ID NO:9:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:9:

Lys Thr Glu Glu Ile Ser Glu Val Lys Met
1               5                   10

(2) INFORMATION FOR SEQ ID NO:10:

(i) SEQUENCE CHARACTERISTICS:
    (A) LENGTH: 10 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:10:

Lys Thr Glu Glu Ile Ser Glu Val Asn Leu
1               5                   10

(2) INFORMATION FOR SEQ ID NO:11:

(i) SEQUENCE CHARACTERISTICS:
    (A) LENGTH: 5 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:11:

Ser Glu Val Asn Leu
1               5

(2) INFORMATION FOR SEQ ID NO:12:

(i) SEQUENCE CHARACTERISTICS:
    (A) LENGTH: 9 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:12:

Cys Gly Gly Glu Ile Ser Val Asn Leu
1               5